United States Patent [19]

Degre

[11] Patent Number: 4,978,528

[45] Date of Patent: Dec. 18, 1990

[54] PROCESS FOR PREVENTING DEGRADATION OF AN ANTI-BACTERIAL COMPOSITION

[75] Inventor: Francois Degre, Saint Affrique, France

[73] Assignee: Bio Serae Laboratoires S.A., Saint Affrique, France

[21] Appl. No.: 165,193

[22] PCT Filed: Jun. 19, 1987

[86] PCT No.: PCT/FR87/00232

§ 371 Date: Apr. 22, 1988

§ 102(e) Date: Apr. 22, 1988

[87] PCT Pub. No.: WO87/07838

PCT Pub. Date: Dec. 30, 1987

[30] Foreign Application Priority Data

Jun. 23, 1986 [FR] France .................................. 86 09166

[51] Int. Cl.$^5$ ........................ A61K 37/50; A61K 33/40
[52] U.S. Cl. .................................... 424/94.4; 424/613; 424/616; 424/609; 424/408; 514/2
[58] Field of Search ................ 424/129, 130, 150, 53, 424/94.4, 48, 488, 609, 613, 616, 408; 514/2

[56] References Cited

U.S. PATENT DOCUMENTS 4,320,116 3/1982 Björck ................................ 424/129
4,473,550 9/1984 Rosenbaum et al. .............. 424/94.4

FOREIGN PATENT DOCUMENTS 0133736 3/1985 European Pat. Off. .
2162063 1/1986 United Kingdom .

*Primary Examiner*—Jacqueline Stone
*Attorney, Agent, or Firm*—Young & Thompson

[57] ABSTRACT

An anti-bacterial composition contains lactoperoxidase, thiocyanate and a native oxygen donor such as a peroxide or an oxidizing enzymatic system. The peroxide or one of the components of the oxidizing enzymatic system is materially isolated from the rest of said composition by a material that is either water-soluble or water-permeable.

11 Claims, No Drawings

PROCESS FOR PREVENTING DEGRADATION OF AN ANTI-BACTERIAL COMPOSITION

BACKGROUND OF THE INVENTION

1. Field of the Invention

The present invention relates to a process for conditioning an anti-bacterial composition, so as to prevent its degradation during storage between manufacture and use. It also relates to an anti-bacterial composition conditioned according to the process.

The anti-bacterial composition to be conditioned according to the process comprising a portion of the present invention, contains lactoperoxidase, thiocyanate, a free oxygen donor and optionally lactoferrin.

2. Description of the Prior Art

It is known that the presence of thiocyanate, free oxygen and lactoperoxidase in an aqueous medium produces a bacterial inhibitor in the form of a monovalent hypothiocyanate ion (OSCN) in acid-base equilibrium with its acid form (HOSCN). (See for example EP No. 0 133 736).

The presence of water is thus necessary to trigger the above-identified reaction. Consequently, the storage of these mixed products can cause degradation. The degree of degradation is a function of the duration of storage, and also of the humidity of the medium.

In patent EP No. 0 133 736, one attempts to overcome this difficulty, either by using a non-aqueous medium, for example glycerine or propylene glycol, or by limiting the quantity of water in the composition (10% maximum by weight). The same patent also teaches the use of silica gel in the composition in the amount of 1 to 5% by weight, for trapping free water in the medium.

In GB No. 2162063, one attempts to overcome this difficulty (without specifically referring to it) by dispersing active materials in a large mass of dry powder. This helps to minimize the chance of active particles encountering each other, first to give off, assuming that the degree of humidity is not 0, hydrogen peroxide and then produce the ions (OSCN) in equilibrium with their acid form (HOSCN).

Once the medium is made aqueous, the mobility of these particles increases by reason of the great quantity of water which facilitates and/or participates, at the same time, in the reaction. The utilization of a large mass of dry powder as a carrier for the active materials, makes the use of such a composition delicate particularly for home use.

In all cases, either for compositions described in EPO No. 133 736, or for those described in GB No. 2 162 063, the risk of degradation of the active materials is present.

It is also known from French patent No. 2 345 940 that the free oxygen donor can be covered by a protective layer whose material becomes permeable and/or dissolves in the basic medium in the intestines. An example of such material is cellulose acetophthalate. The purpose of such specific protection is protection against gastric acidity. The antibacterial composition claimed in this patent, is directed only to the intestines whose medium is basic. This composition cannot be used for treating other regions whose medium is neutral or acidic as for example the mouth, the eyes, the skin and the vagina.

OBJECTS AND SUMMARY OF THE INVENTION

An object of the process forming a portion of the present invention is to condition an anti-bacterial composition containing the system "lactoperoxidase-thiocyanate-free oxygen donor" such that the composition obtained will be useful to treat the intestines as the other regions mentioned above.

The free oxygen donor in this anti-bacterial composition may be an enzymatic oxidant system or an organic or inorganic peroxide.

Another object of said procedure is to provide the possibility of storing such a composition, at any desired concentration for long periods. This while preserving the integrity of the enzymatic activity of said composition.

According to the actual process, the peroxide or one of the components of the enzymatic oxidizing system is substantially isolated from the rest of said composition.

To this end, according to a feature of the invention, the process forming a part thereof is essentially characterized in that the material used to effect this isolation is either hydrosoluble or permeable in aqueous media.

DESCRIPTION OF PREFERRED EMBODIMENTS

The present invention will be better understood by reading the following detailed description accompanied by examples given by way of illustration.

The anti-bacterial properties of the lactoferrin and of the system (lactoperoxidase-thiocyanate-$H_2O_2$) are well known. The lactoferrin captures the iron available in the medium and prevents the bacterial development for which this iron is necessary. The lactoperoxidase plays a role of catalyst to promote the reaction between the thiocyanate and the oxygen donor to produce monovalent hypothiocyanate ions (OSCN) which are anti-bacterial inhibitors. These ions exist in acid-base equilibrium with their acid form (HCSCN). An aqueous medium is necessary for this reaction to take place.

In this description, the peroxide or the enzymatic oxidizing system are called free oxygen donors. In effect, the role of these free oxygen donors is to produce, in the required aqueous medium, molecules of hydrogen peroxide ($H_2O_2$). These latter oxidize, with the aid of the lactoperoxidase, the thiocyanate ions (SCN) to produce hypothiocyanate ions (OSCN).

To ensure production of oxygenated water ($H_2O_2$) and hypothiocyanate ions, an aqueous medium is necessary. These two stages of reaction may be triggered by a humidity content greater than 2%, but at a relatively slow rate. This rate depends on the concentration of molecules taking part in the reactions in the overall mass in which these latter exist. It is evident that if the concentration of these molecules is relatively high, at a humidity permitting the reaction, the speed of the reaction will be greater. On the other hand, at high concentrations of active molecules and at a humidity content lower than that permitting the above-identified reactions, the existence of a strong oxidizer in contact with the enzymes and the proteins may denature the latter.

The process forming a portion of the present invention is based on the physical separation by the hydrosoluble or aqueous medium permeable material, between the enzymes and the proteins and all other components capable of producing free oxygen. The term "all other components" here means anything capable of producing free oxygen in an autonomous fashion.

Accordingly, higher concentrations of enzymes may be used, while avoiding the risk, either of triggering the actions producing an anti-bacterial effect, or of degrading the enzymes themselves.

The needed free oxygen donor, for the above reactions, whose products have the anti-bacterial effect may be, as is known, either organic or inorganic peroxide, or an oxidizing enzymatic system.

The inorganic peroxide may for example be magnesium or sodium peroxide and the organic peroxide may be for example benzoyl peroxide.

The oxidizing enzymatic system may for example be glucose-glucose oxidase or the like (see for example EP No. 0 133 736). All these oxygen donors are described in the literature.

According to the process forming a portion of the present invention, in the case of using an oxidizing enzymatic system, one of these components is isolated from the rest of the anti-bacterial composition; this isolated composition may be glucose for the system glucose, glucose-oxidase, and in the case of using an organic or inorganic peroxide, this peroxide is isolated from the rest of the anti-bacterial composition.

Said separation according to the invention may be effectuated:

either by cladding the granules of peroxide or those of one of the components of the oxidizing enzymatic system, and preferably the substrate, by means of a hydrosoluble protective layer such as for example saccharose, starch, gelatin, carboxymethylcellulose or the like to form microcapsules.

or by grains of dry gel, as for example pectin associated with calcium ions, in which the peroxide or one of the components of the oxidizing enzymatic system is contained, the pore size of the gel network, once humidified, being sufficiently great to permit at least the free passage of peroxide or one of the components of the oxidizing enzymatic system constituted by a substrate and an enzyme.

It is also possible to include in the anti-bacterial composition an enzyme capable of hydrolyzing said gel in the aqueous medium, this permitting destruction of the continuous solid phase and the total liberation of the material on the inside. It is of course evident that pectin may be used as well as any other equivalent material. In the case of using pectin, pectinase is to be used as the enzyme promoting hydrolysis.

To provide these granules of pectin enclosing either the peroxide or one of the components of the oxidizing enzymatic system, the pectin and the substance to be enclosed are dissolved in an aqueous solution which is then showered in fine calibrated droplets into a solution containing calcium ions, the falling droplets forming pearls of gel of the pectin with the calcium ions, the latter enclosing said substance. Said pearls are collected, dried and then mixed with the other components thereby to form the anti-bacterial composition.

It is to be noted that in the case of using an oxidizing enzymatic system, as for example the system glucose, glucose-oxidase, the substrate, which is to say the glucose in this case, may be either provided in its form usable by the enzyme-"glucose-oxidase", or provided by using other products capable of producing it during use.

By way of example, one could use, instead of glucose, starch or maltodextrin, these obviously being associated with suitable enzymes during use to produce glucose according to the reaction:

starch-α-amylase-maltodextrin-amylglucocinase-glucose

In this case, the starch or the maltodextrin is to be isolated from the rest of the anti-bacterial composition which contains, among other things, either α-amylase, or amylglucocinase alone. Likewise one could use, instead of glucose, the system fructose, glucose-isomerase, lactose-β-galactosidase.

To improve the activity of the lactoferrin, in other words to give to the lactoferrin a very great capacity to form complexes with available iron in the medium, one can incorporate in said anti-bacterial composition the bicarbonate of an alkali metal, for example sodium bicarbonate. So that the lactoferrin will have good complexing activity, it should be during its use in a medium containing bicarbonate of about 0.1 to 1% by weight. This concentration of bicarbonate is preferably 0.6% by weight of the medium.

Generally speaking, the quantity of oxygen available to oxidize the thiocyanate should be twice that necessary for this oxidation. For example if one incorporates xM of thiocyanate in the composition, it is necessary to include a sufficient quantity of peroxide or the oxidizing enzymatic system, to produce 2xM of $H_2O_2$.

This appears preferable to ensure the complete utilization of the quantity of thiocyanate.

It is also possible to use lactoferrin having no iron, this lactoferrin being known as apo-lactoferrin.

It should be noted also that it is necessary to avoid substances coacting with the lactoferrin to produce complexes with the iron available in the medium, if these substances in spite of their complexing effect are capable of liberating all or part of the iron rendering it once more available for the bacteria. An example of these substances is tartrate, oxalate or citrate.

The anti-bacterial composition condition according to the process, may be in dry powder form comprised by granules of which some contain the peroxide or one of the components of the enzymatic system clad in a hydrosoluble layer. This layer may be comprised of saccharose, starch, carboxymethylcellulose or the like.

It should be noted that the cladding technique is known per se in the pharmaceutical industry.

The granules to be isolated may be enclosed within granules of gel, as described above or other glucides or hydrosoluble polymers.

In the case of using an oxidizing enzymatic system comprising a substrate and an enzyme, it is preferable to clad the substrate. For example, for the enzymatic system glucose, glucose-oxidase, one clads the glucose by said isolating layer. This composition may be present in conventional forms such as for example sachets, capsules or tablets. Such a composition may be administered orally in the form of capsules or tablets, or it can also be used as vaginal capsules or tablets. In the form of tablets, it may be used as soluble tablets.

It may also be utilized as a solution, after having dissolved it in water just before use.

Once dissolved, it may be used: by oral administration, as a mouthwash, as a gargle, as a therapeutic or spermicidal vaginal douche, or for dermatological, otological, cosmetic or ophthalmological use. Of course the dosages will be suitable for each of these uses. Examples of these dosages will be given later.

For external use, a thickening agent in dry form such as for example carboxymethylcellulose or a known tensioactive agent may be added to said powder, which permits the obtention of a more or less pasty form, once said composition is humidified.

This pasty form may be preferred for example for dermatological use.

The anti-bacterial composition, conditioned according to the invention, may be incorporated in a solid form as for example chewing gum, this gum being chewed and humidified during use.

The anti-bacterial composition, conditioned according to the invention, may be incorporated in foodstuffs for animals.

In the following, there are given several examples of dosages of active materials to be included in the various products thereby to obtain in each case an anti-bacterial composition:

CHEWING GUM (per tablet)

MOUTHWASH (per 25 ml of solution)

GARGLE (per 25 ml of solution)

| GARGLE (per 25 ml of solution) | |
|---|---|
| lactoferrin | 5–50 mg |
| lactoperoxidase | 0.1–1 mg |
| thiocyanate | 5 mg |
| glucose | 25–50 mg |
| glucose oxidase | 0.1–1 mg |

The combination constituted by the glucose and the glucose oxidase may be replaced for example by magnesium peroxide in a quantity of 20 to 100 mg and preferably about 35 mg.

COLLYRIUM (per 5–25 ml)

The quantities of active substances included in the mouthwash per 25 ml may be included in the quantity of solution of 5 to 25 ml for ophthalmologic use.

SOLUTION for dermatological use (per 100 ml of solution)

| SOLUTION for dermatological use (per 100 ml of solution) | |
|---|---|
| lactoferrin | 10–100 mg |
| lactoperoxidase | 3–10 mg |
| thiocyanate | 25–35 mg |
| glucose | 25–100 mg |
| glucose oxidase | 0.1–2 mg |

The combination constituted by glucose and glucose oxidase may be replaced, for example, by magnesium peroxide in an amount varying from 35 to 150 mg.

| SOLUTION for cosmetic use (per 100 ml of solution) | |
|---|---|
| lactoferrin | 5 mg |
| lactoperoxidase | 3 mg |
| thiocyanate | 25 mg |
| MgO$_2$ | 35 mg |
| CAPSULE FOR INTESTINAL INFECTION (per dose) | |
| lactoferrin | 30–150 mg |
| preferably | 60–100 mg |
| lactoperoxidase | 4–10 mg |
| preferably | 6–8 mg |
| glucose | 100–500 mg |
| preferably | 200 mg |
| glucose oxidase | 0.5–2 mg |
| preferably | 2 mg |

The combination constituted by glucose and glucose oxidase may be replaced for example by magnesium peroxide in an amount of 25 to 150 mg and preferably 35 mg.

| TABLET OR CAPSULE for anti-bacterial gynecological use (per dose) | |
|---|---|
| lactoferrin | 5–60 mg |
| lactoperoxidase | 1–10 mg |
| preferably | 4–5 mg |
| thiocyanate | 24–35 mg |
| glucose | 100–200 mg |
| glucose oxidase | 1–2 mg |

The combination comprising glucose and glucose oxidase may be replaced by magnesium peroxide in an amount of 25 to 100 mg.

| TABLET OR CAPSULE for spermicidal usage (per dose) | |
|---|---|
| lactoferrin | as desired |
| lactoperoxidase | 10 mg |
| thiocyanate | 25 mg |
| MgO$_2$ | 35 mg |

It should be noted that the lactoferrin has no known spermicidal effect, it may be incorporated in the composition as a hygienic agent by virtue of its anti-bacterial power.

It should also be noted that the osmotic pressure in the two portions of the ovule containing an anti-bacterial or spermicidal composition should be equalized. This avoids the migration of the active particles from one side to the other of the ovule. Since the osmotic pressure cannot be equalized, the separation of the two portions of the ovule by a hydrosoluble or thermofusible film greatly decreases this migration.

I claim:

1. Process for preventing degradation of an anti-bacterial composition, comprising individual encapsulating granules of a peroxide or one component of an oxidizing enzymatic system with a layer of water-soluble material and combining said encapsulated granules of peroxide or component of an oxidizing enzymatic system with lactoperoxidase and thiocyanate to form an intimate admixture of encapsulated granules, lactoperoxidase and thiocyanate, and where a component of an oxidizing enzymatic system is used also combining the encapsulated granules with another component of the oxidizing enzymatic system, thereby to produce an anti-bacterial composition in which generation of oxygen is prevented prior to use.

2. The process according to claim 1, wherein said combining step further comprises combining the encapsulated peroxide or component of the oxidizing enzymatic system with lactoferrin.

3. The process according to claim 1, wherein said water-soluble material is selected from the group consisting of saccharose, starch and carboxymethylcellulose.

4. The process according to claim 2, wherein said combining step further comprises combining the encapsulated peroxide or component of an oxidizing enzymatic system with a bicarbonate of an alkali metal.

5. The process according to claim 4, wherein said bicarbonate of an alkali metal is sodium bicarbonate.

6. An anti-bacterial composition in dry form, comprising lactoperoxidase, thiocyanate and an oxidizing enzymatic system or a peroxide, wherein granules of the peroxide or granules of one component of the oxidizing enzymatic system are individually encapsulated in a layer of water-soluble material, thereby to prevent premature generation of oxygen by said composition, and wherein said encapsulated granules, lactoperoxidase and thiocyanate are in intimate admixture.

7. The anti-bacterial composition according to claim 6, further comprising lactoferrin.

8. The anti-bacterial composition according to claim 6, wherein said lactoperoxidase, thiocyanate and oxidizing enzymatic system of peroxide are compressed in tablet form.

9. The anti-bacterial composition according to claim 6, wherein said water-soluble material is selected from the group consisting of saccharose, starch and carboxymethylcellulose.

10. Process for preventing degradation of an anti-bacterial composition, comprising encapsulating a peroxide or one component of an oxidizing enzymatic system with a layer of a dried gel comprising pectin associated with calcium ions wherein the gel has a pore size sufficiently great to permit free passage of the peroxide or the component of the oxidizing enzymatic system once the gel has been humidified and combining said encapsulated peroxide or component of an oxidizing enzymatic system with lactoperoxidase and thiocyanate, and where a component of an oxidizing enzymatic system is used also combining the encapsulated component with another component of the oxidizing enzymatic system, thereby to produce an anti-bacterial composition in which generation of oxygen is prevented prior to use.

11. An anti-bacterial composition in dry form, comprising lactoperoxidase, thiocyanate and an oxidizing enzymatic system or a peroxide, wherein the peroxide or one component of the oxidizing enzymatic system is encapsulated in a layer of a dried gel comprising pectin associated with calcium ions wherein the gel has a pore size sufficiently great to permit free passage of the peroxide or the one component of the oxidizing enzymatic system once the dried gel is humidified, thereby to prevent premature generation of oxygen by said composition.

* * * * *